US00RE46422E

(19) United States
(12) Reissued Patent
Foley et al.

(10) Patent Number: US RE46,422 E
(45) Date of Reissued Patent: Jun. 6, 2017

(54) IMAGE GUIDED AWL/TAP/SCREWDRIVER

(71) Applicant: Medtronic Navigation, Inc., Louisville, CO (US)

(72) Inventors: Kevin T. Foley, Germantown, TN (US); Anthony J. Melkent, Germantown, TN (US); Catalina J. Carroll, Memphis, TN (US)

(73) Assignee: Medtronic Navigation, Inc., Louisville, CO (US)

(21) Appl. No.: 14/545,311

(22) Filed: Apr. 20, 2015

Related U.S. Patent Documents

Reissue of:
(64) Patent No.: 6,021,343
Issued: Feb. 1, 2000
Appl. No.: 08/971,126
Filed: Nov. 20, 1997

U.S. Applications:
(63) Continuation of application No. 13/453,709, filed on Apr. 23, 2012, now Pat. No. Re. 45,484, which is a
(Continued)

(51) Int. Cl.
*A61B 17/16* (2006.01)
*A61B 17/88* (2006.01)
(Continued)

(52) U.S. Cl.
CPC ..... *A61B 17/16* (2013.01); *A61B 17/8875* (2013.01); *A61B 34/20* (2016.02);
(Continued)

(58) Field of Classification Search
CPC ..... A61B 17/16; A61B 17/8875; A61B 90/96; A61B 90/36; A61B 34/20; A61B 17/1655;
(Continued)

(56) References Cited

U.S. PATENT DOCUMENTS 1,576,781 A 3/1926 Phillips
1,735,726 A 11/1929 Bornhardt
(Continued)

FOREIGN PATENT DOCUMENTS

CA 964149 3/1975
CA 1336451 1/1988
(Continued)

OTHER PUBLICATIONS

Germano, Isabelle M., "The NeuroStation System for Image-Guided, Frameless Stereotaxy," Neurosurgery, vol. 37, No. 2 Aug. 1995, pp. 348-350.*
(Continued)

*Primary Examiner* — Sara Clarke
(74) *Attorney, Agent, or Firm* — Harness Dickey

(57) ABSTRACT

A trackable medical instrument for use in a computer assisted image guided medical and surgical navigation systems that generate images during medical and surgical procedures, includes a guide member having an emitter array for being tracked by the system and a drive shaft contained within the guide member having a proximal and a distal end, the drive shaft being rotatable within the guide member while being fixable axially inside the guide member, the proximal end of the drive shaft having a first connector for interchangeably receiving at least one drive source, and the distal end having a second connector for interchangeably receiving at least one instrument tip.

21 Claims, 5 Drawing Sheets

Related U.S. Application Data continuation of application No. 10/062,265, filed on Jan. 31, 2002, now Pat. No. Re. 43,328, which is an application for the reissue of Pat. No. 6,021,343.

(51) Int. Cl.

| | |
|---|---|
| ***A61B 19/00*** | (2006.01) |
| ***A61B 17/00*** | (2006.01) |
| ***A61B 90/00*** | (2016.01) |
| ***A61B 34/20*** | (2016.01) |
| ***A61B 90/96*** | (2016.01) |
| *A61B 34/10* | (2016.01) |

(52) U.S. Cl.

CPC ..... *A61B 90/36* (2016.02); *A61B 90/96* (2016.02); *A61B 17/1655* (2013.01); *A61B 34/10* (2016.02); *A61B 2017/0046* (2013.01); *A61B 2034/107* (2016.02); *A61B 2034/2055* (2016.02); *A61B 2034/2072* (2016.02); *A61B 2090/3983* (2016.02)

(58) Field of Classification Search

CPC .... A61B 2017/0046; A61B 2090/3983; A61B 2034/2055; A61B 2034/2072; A61B 2034/107; A61B 34/10

See application file for complete search history.

(56) References Cited

U.S. PATENT DOCUMENTS 2,407,845 A 9/1946 Nemeyer
2,650,588 A 9/1953 Drew
2,697,433 A 12/1954 Zehnder
3,016,899 A 1/1962 Stenvall
3,017,887 A 1/1962 Heyer
3,061,936 A 11/1962 Dobbeleer
3,073,310 A 1/1963 Mocarski
3,109,588 A 11/1963 Polhemus et al.
3,294,083 A 12/1966 Alderson
3,367,326 A 2/1968 Frazier
3,439,256 A 4/1969 Kahne
3,577,160 A 5/1971 White
3,614,950 A 10/1971 Rabey
3,644,825 A 2/1972 Davis, Jr. et al.
3,674,014 A 7/1972 Tillander
3,702,935 A 11/1972 Carey et al.
3,704,707 A 12/1972 Halloran
3,821,469 A 6/1974 Whetstone et al.
3,868,565 A 2/1975 Kuipers
3,941,127 A 3/1976 Froning
3,963,028 A 6/1976 Cooley et al. ..... 128/276
3,983,474 A 9/1976 Kuipers
4,017,858 A 4/1977 Kuipers
4,037,592 A 7/1977 Kronner
4,052,620 A 10/1977 Brunnett
4,054,881 A 10/1977 Raab
4,117,337 A 9/1978 Staats
4,173,228 A 11/1979 Van Steenwyk et al.
4,182,312 A 1/1980 Mushabac
4,202,349 A 5/1980 Jones
4,228,799 A 10/1980 Anichkov et al.
4,256,112 A 3/1981 Kopf et al.
4,262,306 A 4/1981 Renner
4,287,809 A 9/1981 Egli et al.
4,298,874 A 11/1981 Kuipers
4,314,251 A 2/1982 Raab
4,317,078 A 2/1982 Weed et al.
4,319,136 A 3/1982 Jinkins
4,328,548 A 5/1982 Crow et al.
4,328,813 A 5/1982 Ray
4,339,953 A 7/1982 Iwasaki
4,341,220 A 7/1982 Perry
4,346,384 A 8/1982 Raab
4,358,856 A 11/1982 Stivender et al.
4,368,536 A 1/1983 Pfeiler
4,396,885 A 8/1983 Constant
4,396,945 A 8/1983 DiMatteo et al.
4,403,321 A 9/1983 Kruger
4,418,422 A 11/1983 Richter et al.
4,419,012 A 12/1983 Stephenson et al.
4,422,041 A 12/1983 Lienau
4,431,005 A 2/1984 McCormick
4,485,815 A 12/1984 Amplatz et al.
4,506,676 A 3/1985 Duska
4,543,959 A 10/1985 Sepponen
4,548,208 A 10/1985 Niemi
4,571,834 A 2/1986 Fraser et al.
4,572,198 A 2/1986 Codrington
4,583,538 A 4/1986 Onik et al.
4,584,577 A 4/1986 Temple
4,608,977 A 9/1986 Brown
4,613,866 A 9/1986 Blood
4,617,925 A 10/1986 Laitinen
4,618,978 A 10/1986 Cosman
4,621,628 A 11/1986 Brudermann
4,625,718 A 12/1986 Olerud et al.
4,638,798 A 1/1987 Shelden et al.
4,642,786 A 2/1987 Hansen
4,645,343 A 2/1987 Stockdale et al.
4,649,504 A 3/1987 Krouglicof et al.
4,651,732 A 3/1987 Frederick
4,653,509 A 3/1987 Oloff et al.
4,659,971 A 4/1987 Suzuki et al.
4,660,970 A 4/1987 Ferrano
4,672,306 A 6/1987 Thong ..... 324/72.5
4,673,352 A 6/1987 Hansen ..... 433/69
4,688,037 A 8/1987 Krieg
4,701,049 A 10/1987 Beckman et al.
4,705,395 A 11/1987 Hageniers
4,705,401 A 11/1987 Addleman et al.
4,706,665 A 11/1987 Gouda
4,709,156 A 11/1987 Murphy et al.
4,710,708 A 12/1987 Rorden et al.
4,719,419 A 1/1988 Dawley
4,722,056 A 1/1988 Roberts et al. ..... 364/413
4,722,336 A 2/1988 Kim et al.
4,723,544 A 2/1988 Moore et al.
4,727,565 A 2/1988 Ericson
RE32,619 E 3/1988 Damadian
4,733,969 A 3/1988 Case et al.
4,737,032 A 4/1988 Addleman et al.
4,737,794 A 4/1988 Jones
4,737,921 A 4/1988 Goldwasser et al.
4,742,356 A 5/1988 Kuipers
4,742,815 A 5/1988 Ninan et al.
4,743,770 A 5/1988 Lee
4,743,771 A 5/1988 Sacks et al.
4,745,290 A 5/1988 Frankel et al.
4,750,487 A 6/1988 Zanetti
4,753,528 A 6/1988 Hines et al.
4,761,072 A 8/1988 Pryor
4,764,016 A 8/1988 Johansson
4,771,787 A 9/1988 Wurster et al.
4,779,212 A 10/1988 Levy
4,782,239 A 11/1988 Hirose et al.
4,788,481 A 11/1988 Niwa
4,791,934 A 12/1988 Brunnett
4,793,355 A 12/1988 Crum et al.
4,794,262 A 12/1988 Sato et al.
4,797,907 A 1/1989 Anderton
4,803,976 A 2/1989 Frigg et al.
4,804,261 A 2/1989 Kirschen
4,805,615 A 2/1989 Carol
4,809,694 A 3/1989 Ferrara
4,821,200 A 4/1989 Oberg
4,821,206 A 4/1989 Arora
4,821,731 A 4/1989 Martinelli et al.
4,822,163 A 4/1989 Schmidt
4,825,091 A 4/1989 Breyer et al.
4,829,373 A 5/1989 Leberl et al.
4,836,778 A 6/1989 Baumrind et al. ..... 433/69
4,838,265 A 6/1989 Cosman et al.
4,841,967 A 6/1989 Chang et al.

(56) References Cited

U.S. PATENT DOCUMENTS 4,845,771 A 7/1989 Wislocki et al.
4,849,692 A 7/1989 Blood
4,860,331 A 8/1989 Williams et al.
4,862,893 A 9/1989 Martinelli
4,869,247 A 9/1989 Howard, III et al.
4,875,165 A 10/1989 Fencil et al.
4,875,478 A 10/1989 Chen
4,884,566 A 12/1989 Mountz et al.
4,889,526 A 12/1989 Rauscher et al.
4,896,673 A 1/1990 Rose et al.
4,905,698 A 3/1990 Strohl, Jr. et al.
4,923,459 A 5/1990 Nambu
4,931,056 A 6/1990 Ghajar et al.
4,945,305 A 7/1990 Blood
4,945,914 A 8/1990 Allen
4,951,653 A 8/1990 Fry et al.
4,955,891 A 9/1990 Carol
4,961,422 A 10/1990 Marchosky et al.
4,977,655 A 12/1990 Martinelli
4,989,608 A 2/1991 Ratner
4,991,579 A 2/1991 Allen
5,002,058 A 3/1991 Martinelli
5,005,592 A 4/1991 Cartmell
5,013,317 A 5/1991 Cole et al.
5,016,639 A 5/1991 Allen
5,017,139 A 5/1991 Mushabac
5,027,818 A 7/1991 Bova et al.
5,030,196 A 7/1991 Inoue
5,030,222 A 7/1991 Calandruccio et al.
5,031,203 A 7/1991 Trecha
5,042,486 A 8/1991 Pfeiler et al.
5,047,036 A 9/1991 Koutrouvelis
5,050,608 A 9/1991 Watanabe et al. ..... 128/653
5,054,492 A 10/1991 Scribner et al.
5,057,095 A 10/1991 Fabian
5,059,789 A 10/1991 Salcudean
5,078,140 A 1/1992 Kwoh ..... 128/653.1
5,079,699 A 1/1992 Tuy et al.
5,086,401 A 2/1992 Glassman et al.
5,094,241 A 3/1992 Allen
5,097,839 A 3/1992 Allen
5,098,426 A 3/1992 Sklar et al.
5,099,845 A 3/1992 Besz et al.
5,099,846 A 3/1992 Hardy
5,105,829 A 4/1992 Fabian et al.
5,107,839 A 4/1992 Houdek et al.
5,107,843 A 4/1992 Aarnio et al.
5,107,862 A 4/1992 Fabian et al.
5,109,194 A 4/1992 Cantaloube
5,119,817 A 6/1992 Allen
5,142,930 A 9/1992 Allen et al.
5,143,076 A 9/1992 Hardy et al.
5,152,288 A 10/1992 Hoenig et al.
5,160,337 A 11/1992 Cosman
5,161,536 A 11/1992 Vilkomerson et al.
5,178,164 A 1/1993 Allen
5,178,621 A 1/1993 Cook et al.
5,186,174 A 2/1993 Schlöndorff et al. ..... 128/653
5,187,475 A 2/1993 Wagener et al.
5,188,126 A 2/1993 Fabian et al.
5,190,059 A 3/1993 Fabian et al.
5,193,106 A 3/1993 DeSena
5,197,476 A 3/1993 Nowacki et al.
5,197,965 A 3/1993 Cherry et al.
5,198,768 A 3/1993 Keren
5,198,877 A 3/1993 Schulz ..... 356/375
5,207,681 A 5/1993 Ghadjar et al. ..... 606/96
5,207,688 A 5/1993 Carol
5,211,164 A 5/1993 Allen
5,211,165 A 5/1993 Dumoulin et al.
5,211,176 A 5/1993 Ishiguro et al.
5,212,720 A 5/1993 Landi et al.
5,214,615 A 5/1993 Bauer
5,219,351 A 6/1993 Teubner et al.
5,222,499 A 6/1993 Allen et al.
5,224,049 A 6/1993 Mushabac
5,228,442 A 7/1993 Imran
5,230,338 A 7/1993 Allen et al.
5,230,623 A 7/1993 Guthrie et al. ..... 433/72
5,233,990 A 8/1993 Barnea
5,237,996 A 8/1993 Waldman et al.
5,249,581 A 10/1993 Horbal et al.
5,251,127 A 10/1993 Raab ..... 364/413
5,251,635 A 10/1993 Dumoulin et al.
5,253,647 A 10/1993 Takahashi et al.
5,255,680 A 10/1993 Darrow et al.
5,257,636 A 11/1993 White
5,257,998 A 11/1993 Ota et al.
5,261,404 A 11/1993 Mick et al.
5,265,610 A 11/1993 Darrow et al.
5,265,611 A 11/1993 Hoenig et al.
5,269,759 A 12/1993 Hernandez et al.
5,271,400 A 12/1993 Dumoulin et al.
5,273,025 A 12/1993 Sakiyama et al.
5,274,551 A 12/1993 Corby, Jr.
5,279,309 A 1/1994 Taylor et al.
5,285,787 A 2/1994 Machida
5,291,199 A 3/1994 Overman et al.
5,291,889 A 3/1994 Kenet et al.
5,295,483 A 3/1994 Nowacki et al. ..... 128/660.03
5,297,549 A 3/1994 Beatty et al.
5,299,253 A 3/1994 Wessels
5,299,254 A 3/1994 Dancer et al.
5,299,288 A 3/1994 Glassman et al. ..... 395/80
5,300,080 A 4/1994 Clayman et al.
5,305,091 A 4/1994 Gelbart et al.
5,305,203 A 4/1994 Raab ..... 364/413
5,306,271 A 4/1994 Zinreich et al.
5,307,072 A 4/1994 Jones, Jr.
5,309,913 A 5/1994 Kormos et al.
5,315,630 A 5/1994 Sturm et al.
5,316,024 A 5/1994 Hirschi et al.
5,318,025 A 6/1994 Dumoulin et al.
5,320,111 A 6/1994 Livingston
5,325,728 A 7/1994 Zimmerman et al.
5,325,873 A 7/1994 Hirschi et al.
5,329,944 A 7/1994 Fabian et al.
5,330,485 A 7/1994 Clayman et al.
5,333,168 A 7/1994 Fernandes et al.
5,353,795 A 10/1994 Souza et al.
5,353,800 A 10/1994 Pohndorf et al.
5,353,807 A 10/1994 DeMarco
5,359,417 A 10/1994 Muller et al.
5,368,030 A 11/1994 Zinreich et al.
5,371,778 A 12/1994 Yanof et al.
5,375,596 A 12/1994 Twiss et al.
5,377,678 A 1/1995 Dumoulin et al.
5,383,454 A 1/1995 Bucholz ..... 128/653.1
5,385,146 A 1/1995 Goldreyer
5,385,148 A 1/1995 Lesh et al.
5,386,828 A 2/1995 Owens et al.
5,389,101 A 2/1995 Heilbrun et al. ..... 606/130
5,391,199 A 2/1995 Ben-Haim
5,394,457 A 2/1995 Leibinger et al.
5,394,875 A 3/1995 Lewis et al.
5,397,329 A 3/1995 Allen
5,398,684 A 3/1995 Hardy
5,399,146 A 3/1995 Nowacki et al.
5,400,384 A 3/1995 Fernandes et al.
5,402,801 A 4/1995 Taylor
5,408,409 A 4/1995 Glassman et al.
5,413,573 A 5/1995 Koivukangas
5,417,210 A 5/1995 Funda et al.
5,419,325 A 5/1995 Dumoulin et al.
5,423,334 A 6/1995 Jordan
5,425,367 A 6/1995 Shapiro et al.
5,425,382 A 6/1995 Golden et al.
5,426,683 A 6/1995 O'Farrell, Jr. et al.
5,426,687 A 6/1995 Goodall et al.
5,427,097 A 6/1995 Depp
5,429,132 A 7/1995 Guy et al.
5,433,198 A 7/1995 Desai
RE35,025 E 8/1995 Anderton
5,437,212 A 8/1995 Thompson et al. ..... 81/63.1

(56) References Cited

U.S. PATENT DOCUMENTS 5,437,277 A 8/1995 Dumoulin et al.
5,443,066 A 8/1995 Dumoulin et al.
5,443,489 A 8/1995 Ben-Haim
5,444,756 A 8/1995 Pai et al.
5,445,144 A 8/1995 Wodicka et al.
5,445,150 A 8/1995 Dumoulin et al.
5,445,166 A 8/1995 Taylor
5,446,548 A 8/1995 Gerig et al.
5,447,154 A 9/1995 Cinquin et al. ..... 128/653.1
5,448,610 A 9/1995 Yamamoto et al.
5,453,686 A 9/1995 Anderson
5,456,718 A 10/1995 Szymaitis
5,457,641 A 10/1995 Zimmer et al.
5,464,446 A 11/1995 Dreessen et al.
5,469,847 A 11/1995 Zinreich et al.
5,474,558 A 12/1995 Neubardt
5,478,341 A 12/1995 Cook et al.
5,478,343 A 12/1995 Ritter
5,480,422 A 1/1996 Ben-Haim
5,480,439 A 1/1996 Bisek et al.
5,483,961 A 1/1996 Kelly et al.
5,485,849 A 1/1996 Panescu et al.
5,487,391 A 1/1996 Panescu
5,487,729 A 1/1996 Avellanet et al.
5,487,757 A 1/1996 Truckai et al.
5,490,196 A 2/1996 Rudich et al.
5,494,034 A 2/1996 Schlondorff et al.
5,503,416 A 4/1996 Aoki et al.
5,513,637 A 5/1996 Twiss et al.
5,514,146 A 5/1996 Lam et al.
5,515,160 A 5/1996 Schulz et al.
5,517,990 A 5/1996 Kalfas et al. ..... 128/653
5,531,227 A 7/1996 Schneider
5,531,520 A 7/1996 Grimson et al.
5,542,938 A 8/1996 Avellanet et al.
5,543,951 A 8/1996 Moehrmann
5,546,940 A 8/1996 Panescu et al.
5,546,949 A 8/1996 Frazin et al.
5,546,951 A 8/1996 Ben-Haim
5,551,429 A 9/1996 Fitzpatrick et al.
5,558,091 A 9/1996 Acker et al.
5,564,437 A 10/1996 Bainville et al.
5,566,681 A 10/1996 Manwaring et al.
5,568,384 A 10/1996 Robb et al.
5,568,809 A 10/1996 Ben-haim
5,572,999 A 11/1996 Funda et al.
5,573,533 A 11/1996 Strul
5,575,192 A 11/1996 Eggert ..... 81/63.1
5,575,794 A 11/1996 Walus et al.
5,575,798 A 11/1996 Koutrouvelis
5,383,454 B1 12/1996 Bucholz ..... 128/653.1
5,583,909 A 12/1996 Hanover
5,588,430 A 12/1996 Bova et al.
5,590,215 A 12/1996 Allen
5,591,207 A 1/1997 Coleman
5,592,939 A 1/1997 Martinelli
5,595,193 A 1/1997 Walus et al.
5,596,228 A 1/1997 Anderton et al.
5,600,330 A 2/1997 Blood
5,603,318 A 2/1997 Heilbrun et al.
5,611,025 A 3/1997 Lorensen et al.
5,617,462 A 4/1997 Spratt
5,617,857 A 4/1997 Chader et al. ..... 128/653.1
5,619,261 A 4/1997 Anderton
5,622,169 A 4/1997 Golden et al.
5,622,170 A 4/1997 Schulz ..... 128/653
5,627,873 A 5/1997 Hanover et al.
5,628,315 A 5/1997 Vilsmeier et al.
5,630,431 A 5/1997 Taylor
5,636,644 A 6/1997 Hart et al.
5,638,819 A 6/1997 Manwaring et al.
5,640,170 A 6/1997 Anderson
5,642,395 A 6/1997 Anderton et al.
5,643,268 A 7/1997 Vilsmeier et al.
5,645,065 A 7/1997 Shapiro et al.
5,645,545 A 7/1997 Bryant
5,646,524 A 7/1997 Gilboa
5,647,361 A 7/1997 Damadian
5,662,111 A 9/1997 Cosman ..... 128/653.1
5,664,001 A 9/1997 Tachibana et al.
5,674,296 A 10/1997 Bryan et al.
5,676,673 A 10/1997 Ferre et al. ..... 606/130
5,681,260 A 10/1997 Ueda et al.
5,682,886 A 11/1997 Delp et al.
5,682,890 A 11/1997 Kormos et al.
5,690,108 A 11/1997 Chakeres
D387,427 S 12/1997 Bucholz et al. ..... D41/140
5,694,945 A 12/1997 Ben-Haim
5,695,500 A 12/1997 Taylor et al.
5,695,501 A 12/1997 Carol et al.
5,697,377 A 12/1997 Wittkampf
5,702,406 A 12/1997 Vilsmeier et al.
5,711,299 A 1/1998 Manwaring et al.
5,713,946 A 2/1998 Ben-Haim
5,715,822 A 2/1998 Watkins et al.
5,715,836 A 2/1998 Kliegis et al.
5,718,241 A 2/1998 Ben-Haim et al.
5,727,552 A 3/1998 Ryan
5,727,553 A 3/1998 Saad
5,729,129 A 3/1998 Acker
5,730,129 A 3/1998 Darrow et al.
5,730,130 A 3/1998 Fitzpatrick et al.
5,732,703 A 3/1998 Kalfas et al.
5,735,278 A 4/1998 Hoult et al.
5,738,096 A 4/1998 Ben-Haim
5,740,802 A 4/1998 Nafis et al.
5,741,214 A 4/1998 Ouchi et al.
5,742,394 A 4/1998 Hansen
5,744,953 A 4/1998 Hansen
5,748,767 A 5/1998 Raab
5,749,362 A 5/1998 Funda et al.
5,749,835 A 5/1998 Glantz
5,752,513 A 5/1998 Acker et al.
5,755,725 A 5/1998 Druais
RE35,816 E 6/1998 Schulz
5,758,667 A 6/1998 Slettenmark
5,762,064 A 6/1998 Polvani
5,767,669 A 6/1998 Hansen et al.
5,767,960 A 6/1998 Orman
5,769,789 A 6/1998 Wang et al.
5,769,843 A 6/1998 Abela et al.
5,769,861 A 6/1998 Vilsmeier
5,772,594 A 6/1998 Barrick
5,775,322 A 7/1998 Silverstein et al.
5,776,064 A 7/1998 Kalfas et al.
5,782,765 A 7/1998 Jonkman
5,787,886 A 8/1998 Kelly et al.
5,792,055 A 8/1998 McKinnon
5,795,294 A 8/1998 Luber et al.
5,797,849 A 8/1998 Vesely et al.
5,799,055 A 8/1998 Peshkin et al.
5,799,099 A 8/1998 Wang et al.
5,800,352 A 9/1998 Ferre et al.
5,800,535 A 9/1998 Howard, III
5,802,719 A 9/1998 O'Farrell, Jr. et al.
5,803,089 A 9/1998 Ferre et al.
5,807,252 A 9/1998 Hassfeld et al.
5,810,008 A 9/1998 Dekel et al.
5,810,728 A 9/1998 Kuhn
5,810,735 A 9/1998 Halperin et al.
5,810,828 A 9/1998 Lightman et al.
5,820,553 A 10/1998 Hughes
5,823,192 A 10/1998 Kalend et al.
5,823,958 A 10/1998 Truppe
5,828,725 A 10/1998 Levinson
5,828,770 A 10/1998 Leis et al.
5,829,444 A 11/1998 Ferre et al.
5,831,260 A 11/1998 Hansen
5,833,608 A 11/1998 Acker
5,834,759 A 11/1998 Glossop
5,836,954 A 11/1998 Heilbrun et al.
5,840,024 A 11/1998 Taniguchi et al.
5,840,025 A 11/1998 Ben-Haim
5,843,076 A 12/1998 Webster, Jr. et al.

(56) References Cited

U.S. PATENT DOCUMENTS

| | | | |
|---|---|---|---|
| 5,848,967 | A | 12/1998 | Cosman |
| 5,851,183 | A | 12/1998 | Bucholz |
| 5,865,846 | A | 2/1999 | Bryan et al. |
| 5,868,674 | A | 2/1999 | Glowinski et al. |
| 5,868,675 | A | 2/1999 | Henrion et al. |
| 5,871,445 | A | 2/1999 | Bucholz |
| 5,871,455 | A | 2/1999 | Ueno |
| 5,871,487 | A | 2/1999 | Warner et al. |
| 5,873,822 | A | 2/1999 | Ferre et al. |
| 5,882,304 | A | 3/1999 | Ehnholm et al. |
| 5,884,410 | A | 3/1999 | Prinz |
| 5,889,834 | A | 3/1999 | Vilsmeier et al. |
| 5,891,034 | A | 4/1999 | Bucholz |
| 5,891,157 | A | 4/1999 | Day et al. |
| 5,904,691 | A | 5/1999 | Barnett et al. |
| 5,907,395 | A | 5/1999 | Schulz et al. |
| 5,913,820 | A | 6/1999 | Bladen et al. |
| 5,920,395 | A | 7/1999 | Schulz |
| 5,921,992 | A | 7/1999 | Costales et al. |
| 5,923,727 | A | 7/1999 | Navab |
| 5,928,248 | A | 7/1999 | Acker |
| 5,938,603 | A | 8/1999 | Ponzi |
| 5,938,694 | A | 8/1999 | Jaraczewski et al. |
| 5,947,980 | A | 9/1999 | Jensen et al. |
| 5,947,981 | A | 9/1999 | Cosman |
| 5,950,629 | A | 9/1999 | Taylor et al. |
| 5,951,475 | A | 9/1999 | Gueziec et al. |
| 5,951,571 | A | 9/1999 | Audette |
| 5,954,647 | A | 9/1999 | Bova et al. |
| 5,957,844 | A | 9/1999 | Dekel et al. |
| 5,964,796 | A | 10/1999 | Imran |
| 5,967,980 | A | 10/1999 | Ferre et al. |
| 5,967,982 | A | 10/1999 | Barnett |
| 5,968,047 | A | 10/1999 | Reed |
| 5,971,997 | A | 10/1999 | Guthrie et al. |
| 5,976,156 | A | 11/1999 | Taylor et al. |
| 5,980,535 | A | 11/1999 | Barnett et al. |
| 5,983,126 | A | 11/1999 | Wittkampf |
| 5,987,349 | A | 11/1999 | Schulz |
| 5,987,960 | A | 11/1999 | Messner et al. |
| 5,999,837 | A | 12/1999 | Messner et al. |
| 5,999,840 | A | 12/1999 | Grimson et al. |
| 6,001,130 | A | 12/1999 | Bryan et al. |
| 6,006,126 | A | 12/1999 | Cosman |
| 6,006,127 | A | 12/1999 | Van Der Brug et al. |
| 6,013,087 | A | 1/2000 | Adams et al. |
| 6,014,580 | A | 1/2000 | Blume et al. |
| 6,016,439 | A | 1/2000 | Acker |
| 6,019,725 | A | 2/2000 | Vesely et al. |
| 6,021,343 | A | 2/2000 | Foley et al. |
| 6,024,408 | A | 2/2000 | Bello et al. |
| 6,050,724 | A | 4/2000 | Schmitz et al. |
| 6,059,718 | A | 5/2000 | Taniguchi et al. |
| 6,063,022 | A | 5/2000 | Ben-Haim |
| 6,071,288 | A | 6/2000 | Carol et al. |
| 6,073,043 | A | 6/2000 | Schneider |
| 6,076,008 | A | 6/2000 | Bucholz |
| 6,096,050 | A | 8/2000 | Audette |
| 6,104,944 | A | 8/2000 | Martinelli |
| 6,118,845 | A | 9/2000 | Simon et al. |
| 6,122,538 | A | 9/2000 | Sliwa, Jr. et al. |
| 6,122,541 | A | 9/2000 | Cosman et al. |
| 6,131,396 | A | 10/2000 | Duerr et al. |
| 6,139,183 | A | 10/2000 | Graumann |
| 6,147,480 | A | 11/2000 | Osadchy et al. |
| 6,149,592 | A | 11/2000 | Yanof et al. |
| 6,156,067 | A | 12/2000 | Bryan et al. |
| 6,161,032 | A | 12/2000 | Acker |
| 6,165,181 | A | 12/2000 | Heilbrun et al. |
| 6,167,296 | A | 12/2000 | Shahidi |
| 6,172,499 | B1 | 1/2001 | Ashe |
| 6,175,756 | B1 | 1/2001 | Ferre et al. |
| 6,178,345 | B1 | 1/2001 | Vilsmeier et al. |
| 6,194,639 | B1 | 2/2001 | Botella et al. |
| 6,201,387 | B1 | 3/2001 | Govari |
| 6,203,497 | B1 | 3/2001 | Dekel et al. |
| 6,211,666 | B1 | 4/2001 | Acker |
| 6,223,067 | B1 | 4/2001 | Vilsmeier et al. |
| 6,233,476 | B1 | 5/2001 | Strommer et al. |
| 6,236,875 | B1 | 5/2001 | Bucholz et al. |
| 6,246,231 | B1 | 6/2001 | Ashe |
| 6,259,942 | B1 | 7/2001 | Westermann et al. |
| 6,273,896 | B1 | 8/2001 | Franck et al. |
| 6,285,902 | B1 | 9/2001 | Kienzle, III et al. |
| 6,298,262 | B1 | 10/2001 | Franck et al. |
| 6,314,310 | B1 | 11/2001 | Ben-Haim et al. |
| 6,332,089 | B1 | 12/2001 | Acker et al. |
| 6,341,231 | B1 | 1/2002 | Ferre et al. |
| 6,351,659 | B1 | 2/2002 | Vilsmeier |
| 6,381,485 | B1 | 4/2002 | Hunter et al. |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,445,943 | B1 | 9/2002 | Ferre et al. |
| 6,470,207 | B1 | 10/2002 | Simon et al. |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,490,475 | B1 | 12/2002 | Seeley et al. |
| 6,493,573 | B1 | 12/2002 | Martinelli et al. |
| 6,498,944 | B1 | 12/2002 | Ben-Haim et al. |
| 6,516,046 | B1 | 2/2003 | Frohlich et al. |
| 6,527,443 | B1 | 3/2003 | Vilsmeier et al. |
| 6,551,325 | B2 | 4/2003 | Neubauer et al. |
| 6,584,174 | B2 | 6/2003 | Schubert et al. |
| 6,609,022 | B2 | 8/2003 | Vilsmeier et al. |
| 6,611,700 | B1 | 8/2003 | Vilsmeier et al. |
| 6,640,128 | B2 | 10/2003 | Vilsmeier et al. |
| 6,694,162 | B2 | 2/2004 | Hartlep |
| 6,701,179 | B1 | 3/2004 | Martinelli et al. |
| RE43,328 | E | 4/2012 | Foley et al. |
| RE45,484 | E | 4/2015 | Foley et al. |
| 2001/0007918 | A1 | 7/2001 | Vilsmeier et al. |
| 2002/0095081 | A1 | 7/2002 | Vilsmeier |
| 2004/0024309 | A1 | 2/2004 | Ferre et al. |

FOREIGN PATENT DOCUMENTS

| | | | | |
|---|---|---|---|---|
| CA | 1336451 | C | * | 7/1995 |
| DE | 3042343 | A1 | | 6/1982 |
| DE | 3508730 | | | 9/1986 |
| DE | 3717871 | | | 12/1988 |
| DE | 3831278 | A1 | | 3/1989 |
| DE | 3838011 | | | 7/1989 |
| DE | 4213426 | A1 | | 10/1992 |
| DE | 4225112 | C1 | | 12/1993 |
| DE | 4233978 | C1 | | 4/1994 |
| DE | 19715202 | A1 | | 10/1998 |
| DE | 19751761 | A1 | | 10/1998 |
| DE | 19832296 | | | 2/1999 |
| DE | 19747427 | A1 | | 5/1999 |
| DE | 10085137 | | | 11/2002 |
| EP | 0062941 | | | 10/1982 |
| EP | 0119660 | | | 9/1984 |
| EP | 0155857 | A2 | | 9/1985 |
| EP | 0 326 768 | | | 12/1988 |
| EP | 0319844 | A1 | | 6/1989 |
| EP | 0326768 | | | 8/1989 |
| EP | 0350996 | B1 | | 1/1990 |
| EP | 0 501 993 | B1 | | 11/1990 |
| EP | 0419729 | A1 | | 4/1991 |
| EP | 0427358 | | | 5/1991 |
| EP | 0 469 966 | A1 | | 7/1991 |
| EP | 0456103 | | | 11/1991 |
| EP | 0469966 | B1 | | 2/1992 |
| EP | 0501993 | A1 | | 9/1992 |
| EP | 0581704 | | | 2/1994 |
| EP | 0651968 | | | 5/1995 |
| EP | 0655138 | | | 5/1995 |
| EP | 0894473 | B1 | | 2/1999 |
| EP | 0908146 | | | 4/1999 |
| EP | 0930046 | | | 7/1999 |

(56) References Cited

FOREIGN PATENT DOCUMENTS

| | | | |
|---|---|---|---|
| FR | 2417970 | | 9/1979 |
| FR | 2618211 | B1 | 11/1991 |
| GB | 2094590 | | 9/1982 |
| GB | 2164856 | A | 4/1986 |
| JP | 62327 | | 6/1983 |
| JP | 61-94639 | A | 10/1984 |
| JP | 63240851 | A | 10/1988 |
| JP | 2765738 | B2 | 4/1991 |
| JP | 3267054 | | 11/1991 |
| WO | WO-8809151 | | 12/1988 |
| WO | WO-8905123 | A1 | 6/1989 |
| WO | WO 90/05494 | | 5/1990 |
| WO | WO-9005494 | A1 | 5/1990 |
| WO | WO-9103982 | | 4/1991 |
| WO | WO-9104711 | | 4/1991 |
| WO | WO 91/07726 | | 5/1991 |
| WO | WO-9107726 | A1 | 5/1991 |
| WO | WO-9203090 | | 3/1992 |
| WO | WO 92/06645 | | 4/1992 |
| WO | WO-9206645 | A1 | 4/1992 |
| WO | WO-9404938 | A1 | 3/1994 |
| WO | WO-9423647 | | 10/1994 |
| WO | WO-9424933 | | 11/1994 |
| WO | WO-9507055 | | 3/1995 |
| WO | WO 96/11624 | | 4/1996 |
| WO | WO-9611624 | A2 | 4/1996 |
| WO | WO-9632059 | A1 | 10/1996 |
| WO | WO97/15234 | | 5/1997 |
| WO | WO-9715234 | A1 | 5/1997 |
| WO | WO-9736192 | A1 | 10/1997 |
| WO | WO-9749453 | A1 | 12/1997 |
| WO | WO-9808554 | | 3/1998 |
| WO | WO-9838908 | | 9/1998 |
| WO | WO-9915097 | | 4/1999 |
| WO | WO-9921498 | A1 | 5/1999 |
| WO | WO-9923956 | | 5/1999 |
| WO | WO-9926549 | | 6/1999 |
| WO | WO-9929253 | | 6/1999 |
| WO | WO-9933406 | | 7/1999 |
| WO | WO-9937208 | A1 | 7/1999 |
| WO | WO-9938449 | | 8/1999 |
| WO | WO-99/27839 | A3 | 10/1999 |
| WO | WO-9952094 | | 10/1999 |
| WO | WO-9960939 | | 12/1999 |
| WO | WO-0130437 | | 5/2001 |

OTHER PUBLICATIONS

Alignment Procedure for the PixSys Two-Emitter Offset Probe for the Sac Gp-8-3d Sonic Digitizer, PixSys, Jul. 2, 1992, pp. 1- 4.*

Bucholz et al., Richard D. Intraoperative localization using a three dimensional optical digitizer Proceeding of Clinical Applications of Modern Imaging Technology, Spie vol. 1894 (Jan. 19, 1993), pp. 312-322.*

Adams et al., Computer-Assisted Surgery, IEEE Computer Graphics & Applications, pp. 43-51, (May 1990).

Adams, L., et al., "Aide Au Reperage Tridimensionnel Pour La Chirurgie de la Base du Crane," Innov. Tech. Biol. Med., vol. 13, No. 4, pp. 409-424, 1992.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology .Copyrgt. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, pp. 137-145 (undated.

(56) References Cited

OTHER PUBLICATIONS

Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, pp. 193-211 (undated.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, et al., "Reference-Display System for the Integration of CT Scanning and the Operating Microscope", Proceedings of the Eleventh Annual Northeast Bioengineering Conference, Mar. 14-15, 1985, pp. 252-254.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kall, B., The Impact of Computer and lmgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique for Accurate Transpedicular Screw Fixation Using CT Data and a 3-D Optical Localizer," TIMC, Faculte de Medecine de Grenoble.
Lavallee et al., "Image guided operating robot: clinical application in stereotactic neurosurgery," Proceedings of the 1992 IEEE Internation Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.

(56) References Cited

OTHER PUBLICATIONS

Lavallee, "VI Adaption de la Methodologie a Quelques Applications Cliniques," Chapitre VI, pp. 133-148.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753761 (Oct. 1998).
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337, pp. 86-96.
Ng, W.S. et al., Robotic Surgery—A First-Hand Experience in Transurethral Resection of the Prostate Surgery, IEEE Eng. in Med. and Biology, pp. 120-125 (Mar. 1993).
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans Inst. Mc, vol. 17, No. 5, 1995, pp. 251-264.
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al., "CT-Guided 'Real Time' Stereotaxy," ACTA Neurochirurgica, 1989.
Reinhardt, H., et al., A Computer-Assisted Device for Intraoperative CT-Correlated Localization of Brain Tumors, pp. 51-58 (1988).
Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).
Reinhardt, Hans. F., Neuronavigation: A Ten-Year Review, Neurosurgery, pp. 329-341 (undated).
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Simon, D.A., Accuracy Validation in Image-Guided Orthopaedic Surgery, Second Annual Intl. Symp. on Med. Rob. an Comp-Assisted surgery, MRCAS '95, pp. 185-192 (undated).
Skip Jacques, et al., "A Computerized Microstereotactic Method to Approach, 3-Dimensionally Reconstruct, Remove and Adjuvantly Treat Small CNS Lesions," Meeting of the Amer. Soc. Stereotactic & Functional Neurosurgery, Houston 1980, Appl.Neurophysiol. 43: 176-182 (1980).
Smith et al., "Computer Methods for Improved Diagnostic Image Display Applied to Stereotactic Neurosurgery," Automedical, vol. 14, 1992, pp. 371-382 (4 unnumbered pages).
Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
Thompson, et al., A System for Anatomical and Functional Mapping of the Human Thalamus, Computers and Biomedical Research, vol. 10, pp. 9-24 (1977).
Trobraugh, J.W., et al., Frameless Stereotactic Ultrasonography: Method and Applications, Computerized Medical Imaging and Graphics, vol. 18, No. 4, pp. 235-246 (1994).
Viant et al., "A Computer Assisted Orthopaedic System for Distal Locking of Intramedullary Nails," Proc. of MediMEC '95, Bristol, 1995, pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Weese et al., "An Approach to 2D/3D Registration of a Vertebra in 2D X-ray Fluoroscopies with 3D CT Images," pp. 119-128.
"Prestige Cervical Disc System Surgical Technique", Medtronic Sofamor Danek USA, Inc., 46 pgs. 2006.
Adams, L., et al., "Aide Au Reperage Tridimensionnel Pour La Chirurgie de la Base du Crane," Innov. Tech. Biol. Med., vol. 13, No. 4 pp. 409-424, 1992.
Adams et al., "Orientation Aid for Head and Neck Surgeons," Innov. Tech. Biol. Med., vol. 13, No. 4, 1992, pp. 409-424.
Bucholz, et al., Halo vest versus spinal fusion for cervical injury: evidence from an outcome study, J. Neurosurg., vol. 70, Abstract, one page. Jun. 1989.

(56) References Cited

OTHER PUBLICATIONS

Heilbrun, M.P., Computed Tomography—Guided Stereotactic Systems, Clinical Neurosurgery, Chapter 31, pp. 564-581 (1983).
Laitenen: The Laitenen Stereotactic System; STT, 5 pages, 1980.
Pixsys 3-D Digitizing Accessories, 2 unnumbered pages.
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Shelden et al., "Development of a computerized microsteroetaxic method for localization and removal of minute CNS lesions under direct 3-D vision," J. Neurosurg., vol. 52, 1980, pp. 2127.
Smith et al., "The Neurostation™—Highly Accurate, Minimally Invasive Solution to Frameless Stereotactic Neurosurgery," Computerized Medical Imaging and Graphics, vol. 18, Jul.-Aug. 1994, pp. 247-256.
Richard D. Bucholz, M.D. and K. Charles Cheung, M.D., "Halo vest versus spinal fusion for cervical injury: evidence from an outcome study," J. Neurosurg 70:884-892, Jun. 1989.
W. Krybus, et al., "Navigation Support for Surgery by Means of Optical Position Detection," p. 362-366, 1990.
Kurt R. Smith and Richard D. Bucholz, "Computer Methods for Improved Diagnostic Image Display Applied to Stereotactic Neurosurgery," Stereotactic Neurosurgery Display, vol. 14, pp. 371-382, 1992.
Offset Probe for SAC GP8-3d Digitizer, 2 pages, not dated.
"3-D Digitizing Accessories," PixSys, Jul. 2, 1996, 6 pages.
Richard D. Bucholz, M.D., et al., "Poster #1120, Use of an Intraoperative Optical Digitizer in a System for Free-Hand Stereotactic Surgery," Scientific Program, Am. Assoc. of Neurological Surgeons 1992 Annual Meeting, pp. 284-285, Apr. 16, 1992.

* cited by examiner

IMAGE GUIDED AWL/TAP/SCREWDRIVER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a reissue of U.S. Pat. No. 6,021,343 issued on Feb. 1, 2000 and also claims benefit under 35 U.S.C. §120 as a continuation of currently pending U.S. patent application Ser. No. 13/453,709, filed on Apr. 23, 2012; which is also a reissue of U.S. Pat. No. 6,021,343 issued on Feb. 1, 2000; which claims benefit under 35 U.S.C. §120 as a continuation of U.S. Pat. No. Re. 43,328, which is also a reissue of U.S. Pat. No. 6,021,343 issued on Feb. 1, 2000. The disclosures of the above applications are incorporated herein by reference.*

BACKGROUND OF THE INVENTION

1. Field of the Invention

The present invention relates generally to computer assisted image guided medical and surgical navigation systems that generate images during medical and surgical procedures indicating the relative position of various body parts, surgical implants, and instruments. In particular, the present invention relates to an instrument for use in an image guided surgery navigation system that enables the system to track both the depth and the trajectory of the instrument during surgery.

2. Background of Related Art

Computer assisted image guided medical and surgical navigation systems are known and used to generate images in order to guide a doctor during a surgical procedure. Such systems are disclosed, for example, in U.S. Pat. No. 5,383,454 to Bucholz; PCT application Ser. No. PCT/US94/04530 (Publication No. WO 94/24933) to Bucholz; and PCT application Ser. No. PCT/US95/12984 (Publication No. WO 96/11624) to Bucholz et al., incorporated herein by reference.

In general, these image guided systems use images of a body part, such as CT scans, taken before surgery to generate images on a display, such as a CRT monitor screen, during surgery for representing the position of a surgical instrument with respect to the body part. The systems typically include tracking devices such as, for example, an LED array mounted on a surgical instrument as well as a body part, a digitizer to track in real time the position of the body part and the instrument used during surgery, and a monitor screen to display images representing the body and the position of the instrument relative to the body part as the surgical procedure is performed.

There is a need in the art for a surgically navigable tool for use with these image guided systems that is simple to use and manipulate, that enables the computer tracking system to track both the trajectory of the instrument and the depth that the instrument is inserted into the body, and that is easily interchangeable with alternative drive sources such as a ratcheting handle or other instruments such as awls, taps, and screwdrivers.

SUMMARY OF THE INVENTION

It is therefore an object of the invention to provide an image guided medical instrument whose tip and trajectory can be simultaneously tracked.

It is a further object of the invention to provide an image guided medical instrument capable of generating a signal representing the trajectory and the depth of the tip of the instrument.

It is a still further object of the invention to provide an image guided medical instrument that may easily be used with any number of different tips and handles.

It is another object of the invention to provide an image guided medical instrument that is of relatively simple construction and relatively easy to use.

Additional objects and advantages of the invention will be set forth in the description which follows and, in part, will be obvious from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a trackable medical instrument for use in a computer assisted image guided surgery system having a digitizer for tracking the position of the instrument in three dimensional space and a display providing an indication of the position of the instrument with respect to images of a body part taken preoperatively. The instrument includes a guide member having an emitter array mounted thereon for being tracked by the digitizer, and a drive shaft contained within the guide member, the drive shaft having a proximal and a distal end, the drive shaft being rotatable within the guide member while being fixable axially within the guide member, the proximal end of the drive shaft having a first connector for interchangeably receiving at least one drive source, and the distal end having a second connector for interchangeably receiving at least one instrument tip. The instrument may further include at least one instrument tip for connection to the distal end of the drive shaft and a drive handle for connection to the proximal end of the drive shaft for transmitting torque to the instrument tip to cause rotation of the instrument tip.

In another aspect of this invention, the instrument may further include a sensor which senses the removal and the connection of an instrument tip to the instrument. The sensor may be an electromechanical switch on the guide member.

It is to be understood that both the foregoing general description and the following detailed description are exemplary and explanatory and are not restrictive of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
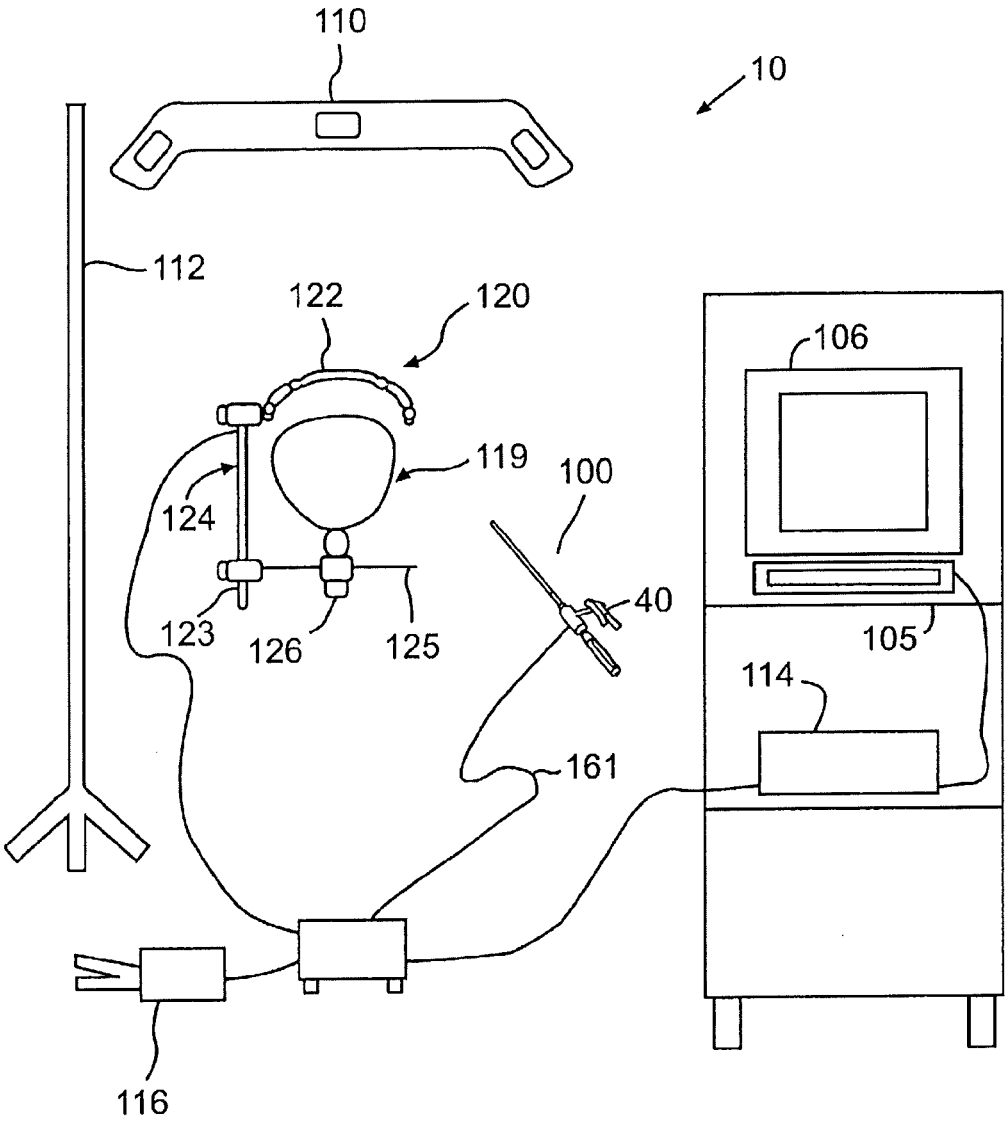
FIG. 1 is a schematic front view of a computer assisted image guided surgery system used with an instrument according to the present invention.

Reference will now be made in detail to the present preferred embodiments of the invention, examples of which are illustrated in the accompanying drawings. Wherever possible, the same reference numbers are used in the drawings and the description to refer to the same or like parts.

The medical instrument of the present invention is shown generally at 10 in FIG. 1. Instrument 100 can be used in many known computer assisted image guided surgical navigation systems such the system shown in FIG. 1 and disclosed in PCT application Ser. No. PCT/US95/12984 (Publication No. WO 96/11624) to Bucholz et al., incorporated herein by reference. A computer assisted image guided surgery system, shown at 10, generates an image for display on a monitor 106 representing the real time position of a body part and the position of instrument 100 relative to the body part.

An image may be generated on monitor 106 from an image data set stored in a controller, such as computer 108, usually generated preoperatively by some scanning technique such as by a CAT scanner or by magnetic resonance imaging. The image data set and the image generated have reference points for at least one body part. The reference points for the particularly body part have a fixed spatial relation to the particular body part.

System 10 also generally includes a processor for processing image data, shown as digitizer control unit 114. Digitizer control unit 114 is connected to monitor 106, under control of computer 108, and to instrument 100. Digitizer 114, in conjunction with a reference frame arc 120 and a sensor array 110 or other known position sensing unit, tracks the real time position of a body part, such as a cranium shown at 119 clamped in reference frame 120, and an instrument 100. Reference frame 120 has emitters 122 or other tracking means that generate signals representing the position of the various body reference points. Reference frame 120 is fixed spatially in relation to a body part by a clamp assembly indicated generally at 124, 125, and 126. Instrument 100 also has a tracking device shown as an emitter array 40 which generates signals representing the position of the instrument during the procedure.

Sensor array 110, mounted on support 112, receives and triangulates the signals generated by emitters 122 and emitter array 40 in order to identify during the procedure the relative position of each of the reference points and the instrument. Digitizer 114 and computer 108 may then modify the image date set according to the identified relative position of each of the reference points during the procedure. Computer 108 may then generate an image data set representing the position of the body elements and the instrument during the procedure. System 10 may also include a foot switch 116 connected to instrument 100 and digitizer 114 for controlling operation of the system. The structure and operation of an image guided surgery system is well known in the art and need not be discussed further here.

Figure 2:
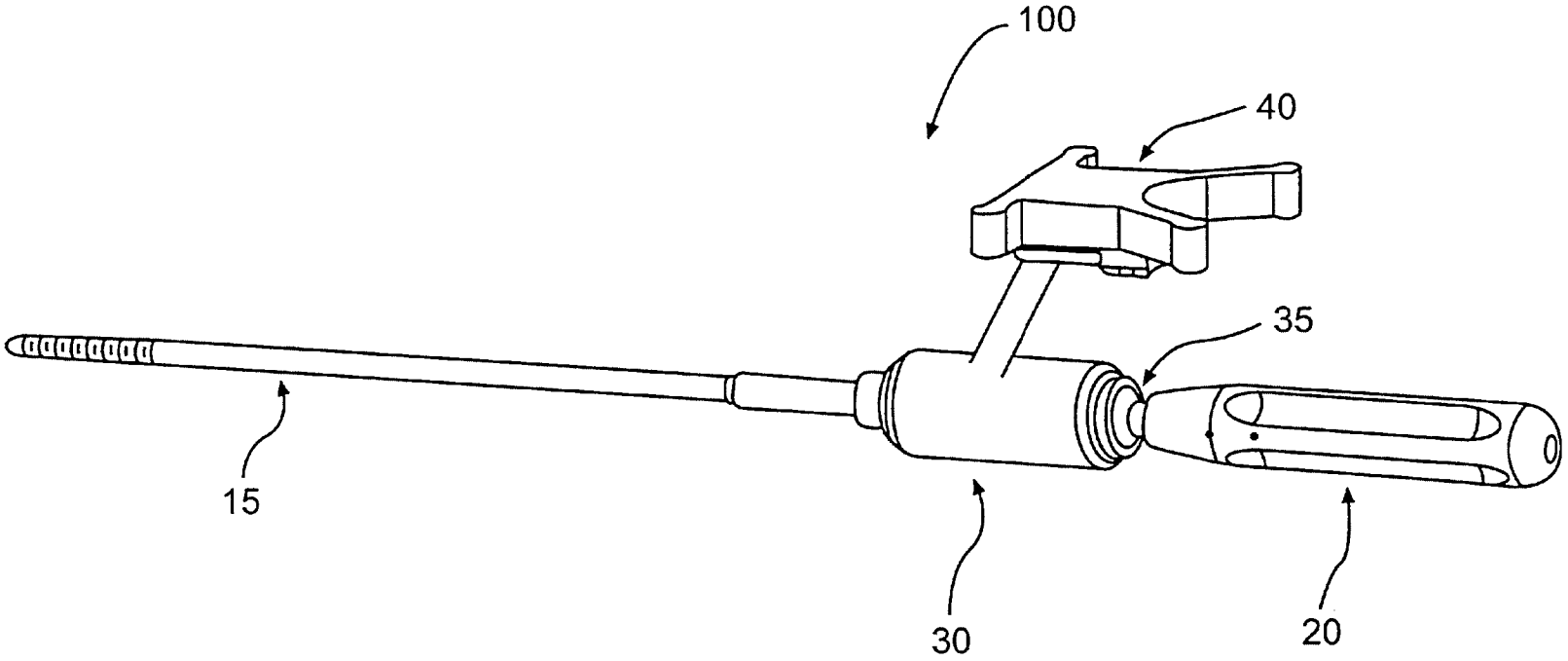
FIG. 2 is a perspective view of an instrument according to the present invention.
Figure 3:
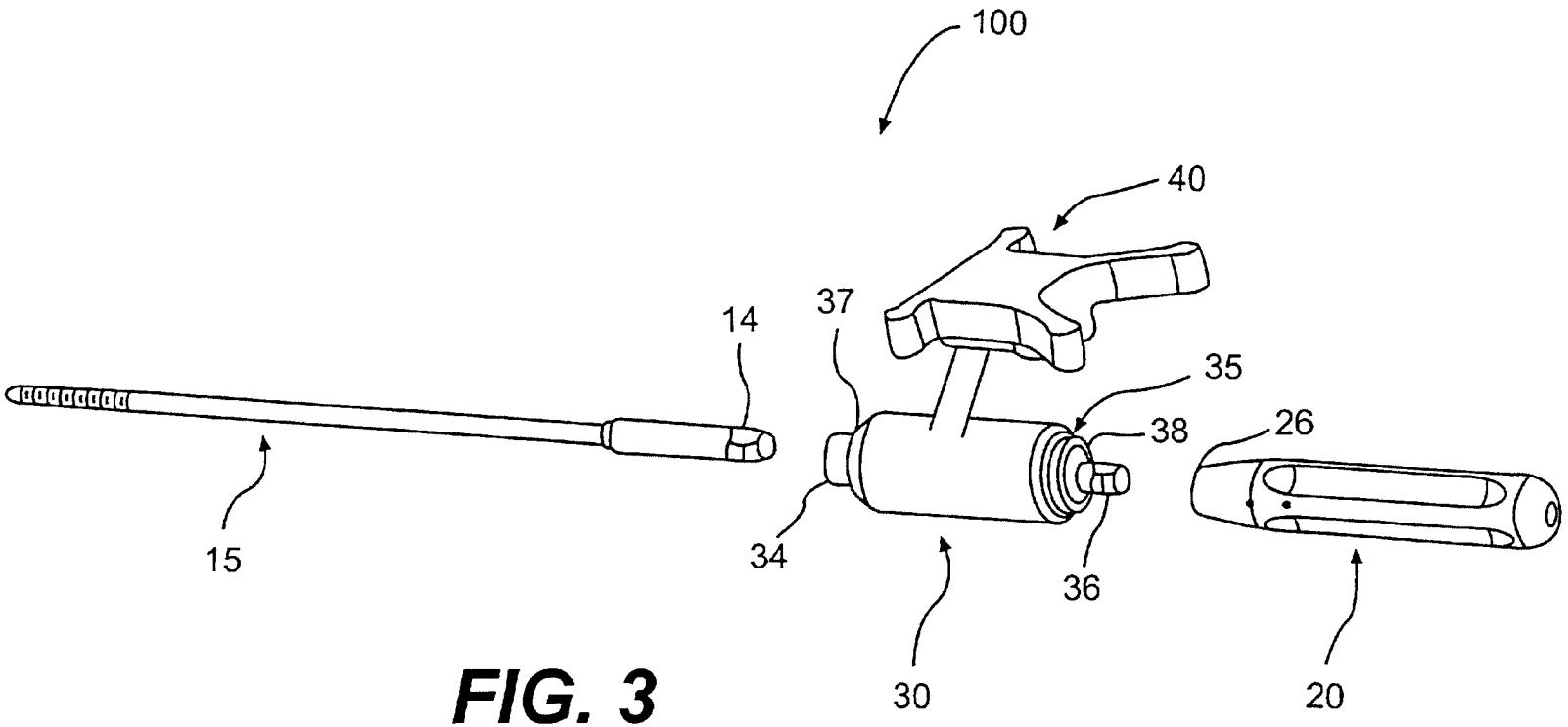
FIG. 3 is an exploded view of the instrument shown in FIG. 2.

Referring to FIGS. 2 and 3, an instrument according to the present invention is shown at 100. Instrument 100 includes a guide member 30, an interchangeable instrument tip 15, and an interchangeable driving handle 20.

Figure 5:
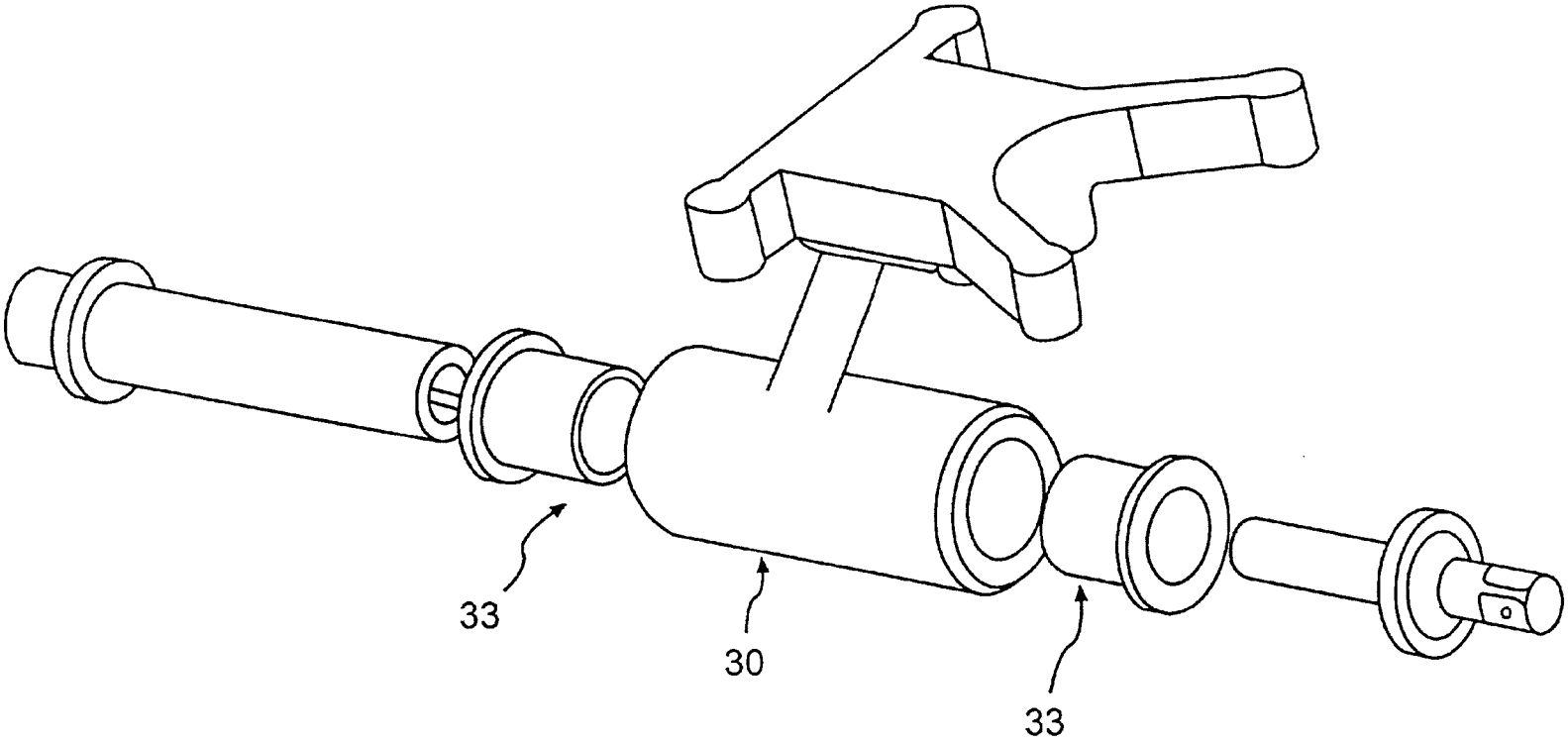
FIG. 5 is an exploded view of the portion of the instrument shown in FIG. 4.

A drive shaft 35 is housed within guide member 30 and is removably connected to an end, here the proximal end 37, to surgical instrument tip 15 and at the other end, here the distal end 38, to driving handle 20 such that torque applied manually or by motorized means to drive handle 20 is transmitted to drive shaft 35 which in turn is transmitted to tip 15. Drive shaft 35, while it could be extractable such as for service, is fixable axially in relation to guide member 30, but is rotatable within guide member 30. As shown in FIG. 5, bushings 33 may be provided at each end of guide member 30 to ensure smooth motion between drive shaft 35 and guide member 30. Guide member 30 is preferably made of stainless steel, but can also be made of titanium, aluminum or plastic. Shaft 35 is preferably made from stainless steel, titanium, or aluminum.

Figure 4:
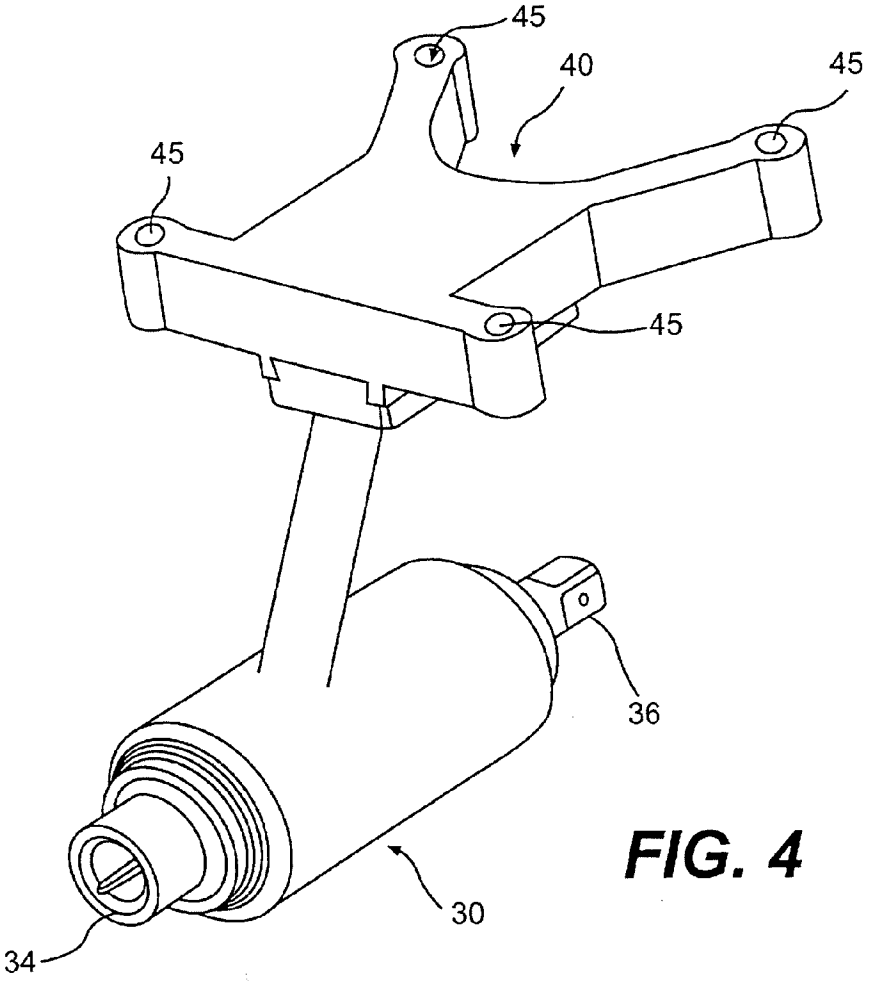
FIG. 4 is a view of a portion of the instrument shown in FIG. 2.

Instrument 100 further includes a tracking device such as emitter array 40 attached to guide member 30 for tracking the location and trajectory of instrument 100. As shown in FIG. 4, array 40 is equipped with a plurality of emitters or tracking means 45, preferably four emitters, for generating a signal representing the trajectory of instrument 100 and the depth of instrument tip 15. Preferably emitters 43 are light emitting diodes; however, other tracking devices known in the art capable of being tracked by a corresponding sensor array are within the scope of the invention. For purposes of illustration, not limitation, the tracking device may generate signals actively such as with acoustic, magnetic, electromagnetic, radiologic, and micropulsed radar systems, or passively such as with reflective surfaces.

Drive handle 20 and instrument tip 15 are shown as modular units that can be attached to drive shaft 35 with corresponding and interlocking male and female socket joints. As shown in FIGS. 3 and 4, drive shaft 35 has a female socket joint 34 for connection with a male socket 14 on tip 15, and drive shaft 35 has a male socket joint 36 for connection with a female socket joint 26 on drive handle 20. With the use of male and female socket joints, various instrument tips and various type and sized drive handles can be easily interchangeable. Instrument tip 15 could be any of a variety of instruments used in surgery such as taps, awls, and shaped tools for interacting with a work piece, such as a screwdriver for driving screws. Drive handle 20 could be any number of existing or specially designed handles and could be ratcheting, nonratcheting or motorized. Instrument tip 15 and drive handle 20 could also be permanently attached to drive shaft 35. Other suitable connection means are within the scope of the invention as well.

In operation, torque applied to drive handle 20 is transmitted through drive shaft 35 to instrument tip 15. Because drive shaft 35 is fixed axially in relation to guide member 30, guide member 30 can remain stationary while drive shaft 35 rotates without translating along the axis of drive shaft 35. The relationship between array 40 and the axis of drive shaft 35, therefore, remains constant. Instrument tip 15 is also fixed axially in relation guide member 30. As a result, the relationship between array 40 and instrument tip 15 also remains constant. Because the relationship between array 40 and tip 15 is constant, the signals emitted by emitters 45 can be used by the computer assisted image guided surgical navigation system to inform the surgeon of the position of instrument 100, indicating both the trajectory or orientation in three dimensional space of instrument 100 and the length of travel along the trajectory, i.e., the depth instrument tip 15 has been inserted into a body part.

It should be recognized that other variations or modifications may be made to provide an instrument that has an emitter array fixed axially relative to the instrument tip while allowing the instrument tip to rotate relative to the emitter array. For example, guide member 30 may also be integral with instrument tip 15 and/or drive handle 20. The array could then be fixed axially relative to the instrument and means could be provided to allow rotation of the instrument relative to the array.

As discussed above, a variety of different instrument tips may be easily interchanged on instrument 100. To use these different instrument tips, information concerning the dimensions of the different tips may be entered into computer 108. As a result, computer 108 can process the various image data for the specific instrument tip being used so that system 10 tracks the depth of the tip being used or, in the case of a screwdriver, so that system 10 tracks the depth of the screw being inserted.

System 10 may also be provided with a mechanism to prevent the system from operating after a new tip has been connected until computer 108 has been recalibrated. For example, an electromechanical switch, or other suitable sensors, could be provided on instrument 100 to provide a signal to computer 108 indicating that instrument tip 15 has been removed from instrument 100 or that a new instrument tip 15 has been coupled to instrument 100. The switch is preferably a micro switch but can be embodied by any suitable electrical or electromechanical device or sensing device capable of providing a signal in response to attachment or detachment at a particular point on guide member 30 or tip 15.

The switch may be automatically actuated when tip 15 is removed or coupled to instrument 100. Computer 108 may be operably connected to the switch, such as through cable 161, and is responsive to the operation of the switch. Alternatively, if a wireless instrument is used such as one with passive reflective surfaces in place of LED emitters, any suitable form of communication known in the art can be used. An alarm or other indication of some type, such as a message or display on monitor 106, may be generated by computer 108 indicating to the user that tip 15 has been changed. The computer 108 may further prevent the system from operating until the system has been recalibrated for the new instrument tip. Recalibration may be accomplished by touching the instrument tip to a known reference point. Recalibration of the instrument tip can be positively confirmed by means of a light emission from the emitter array 40 detected by sensor array 110 and triangulated to determine the position of the instrument tip. Alternatively, the dimensions of the instrument or tool type may be entered into computer 108 or selected from a pre-programmed list of tool dimensions or tool types. Further, recalibration could be accomplished by a fiber optic device for reading a bar code on the instrument tip, or by any other suitable recalibration technique.

It will also be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

[1. A trackable medical instrument for use in a computer assisted image guided surgery system having a digitizer for tracking the position of the instrument in three dimensional space and a display providing an indication of the position of the instrument with respect to images of a body part take preoperatively, the instrument comprising:

a guide member having an emitter array mounted thereon for being tracked by a digitizer; and a drive shaft contained within the guide member, the drive shaft having a longitudinal axis and a proximal and a distal end, the drive shaft being rotatable within the guide member while being fixable within the guide member in a direction of the longitudinal axis, the proximal end of the drive shaft having a first connector for interchangeably receiving at least one drive source for transmitting torque to the drive shaft causing rotation of the drive shaft relative to the guide member, and the distal end having a second connector for interchangeably receiving at least one instrument tip.]

[2. The instrument according to claim 1, further comprising at least one instrument tip for removable connection to the distal end of the drive shaft.]

[3. The instrument according to claim 2, wherein the at least on drive source comprises a drive handle for removable connection to the proximal end of the drive shaft for transmitting torque to the drive shaft and the instrument tip to cause rotation of the instrument tip.]

[4. The instrument according to claim 3, wherein the drive handle and the drive shaft include a male-female socket joint to removably connect the drive shaft to the drive handle.]

[5. The instrument according to claim 3, wherein the drive handle includes a ratchet.]

[6. The instrument according to claim 3, wherein the drive handle includes a motor for imparting torque to the drive shaft.]

[7. The instrument according to claim 2, wherein the instrument tip and the drive shaft include a male-female socket joint to removably connect the drive shaft to the instrument tip.]

[8. The instrument according to claim 2, wherein the instrument tip is an awl.]

[9. The instrument according to claim 2, wherein the instrument tip is a tap.]

[10. The instrument according to claim 2, wherein the instrument tip has a shaped end for mating with a workpiece to be rotated by said drive shaft.]

[11. The instrument according to claim 2, wherein the instrument tip is a drill bit.]

[12. The instrument according to claim 1, wherein the emitter array includes at least one LED array for emitting light signals.]

[13. The instrument according to claim 12, wherein the LED array includes a base and a plurality of LED emitters disposed on the base.]

[14. The instrument according to claim 1, wherein at least one bushing is provided in the guide member to reduce friction between the guide member and drive shaft.]

[15. The instrument according to claim 1, wherein the instrument includes a sensor which senses the removal and connection of an instrument tip to the instrument.]

[16. The instrument according to 15, wherein the sensor includes an electromechanical switch on the guide member electrically connected to the system.]

[17. A trackable medical instrument for use in a computer assisted image guided surgery system having a digitizer for receiving signals representing a position of the instrument during surgery, a computer for processing the signals received, and a display for providing an image representing the position of the instrument in three dimensional space during surgery, the instrument comprising:

guiding means for guiding the instrument in three dimensional space, the guiding means including signaling means for providing a signal representing the trajectory of the instrument and the location of the instrument; and driving means for driving the instrument contained within the guiding means, the driving means having a longitudinal axis and being fixable in relation to the guiding means in a direction of the longitudinal axis while being rotatable in relation to the guiding means, the driving means having a first end adapted to interchangeably receive at least one medical instrument tip and an opposite end adapted to interchangeably receive at least one drive source.]

[18. The instrument according to claim 17, wherein the instrument includes a sensing means for sensing the removal and the connection of an instrument tip to the instrument.]

[19. The instrument according to 18, wherein the sensing means includes an electromechanical switch on the guiding means connected to the means for processing.]

[20. The instrument according to claim 17, wherein the guiding means comprises a housing for receiving the driving means, the driving means being rotatable within the housing while being retained axially within the housing.]

[21. The instrument according to claim 20 wherein the signaling means comprises an LED array.]

[22. The instrument according to claim 21, further comprising an instrument tip for connection to the first end of the driving means.]

[23. The instrument according to claim 22, further comprising a drive handle for connection to the opposite end of the driving means for transmitting torque to the instrument tip to cause rotation of the instrument tip.]

[24. The instrument according to claim 20, wherein the driving means comprises a drive shaft having mating connectors on both ends for connection to corresponding connectors disposed on an instrument tip and a drive source.]

[25. The instrument according to claim 24, wherein at least one bushing is provided between the housing and the drive shaft to reduce friction between the guide handle and drive shaft.]

[26. The instrument according to claim 22, wherein the instrument tip is an awl.]

[27. The instrument according to claim 22, wherein the instrument tip is a tap.]

[28. The instrument according to claim 22, wherein the instrument tip has a shaped end for mating with a workpiece.]

[29. A trackable medical instrument for use in a computer assisted image guided surgery system having a digitizer for tracking the position of the instrument in three dimensional space and a display providing an indication of the position of the instrument with respect to images of a body part take preoperatively, the instrument comprising:

a guide member having an emitter array mounted thereon for being tracked by a digitizer;

a drive shaft contained within the guide member, the drive shaft having a longitudinal axis and a proximal and a distal end, the drive shaft being rotatable within the guide member while being fixable within the guide member in a direction of the longitudinal axis;

an instrument tip extending from the proximal end of the drive shaft; wherein the instrument tip rotates freely relative to the guide member while being fixable axially relative to the guide member; and a drive handle extending from the distal end of the drive shaft for guiding the instrument, including the guide member, and for imparting rotary motion to the drive shaft and the instrument tip independent of the guide member.]

[30. The instrument according to claim 29, further comprising a proximal coupler for interchangeably coupling the drive source to the drive shaft.]

[31. The instrument according to claim 30, wherein the proximal coupler comprises a male-female socket joint disposed on the drive shaft and the drive source to removably connect the drive source to the drive shaft.]

[32. The instrument according to claim 29, wherein the drive handle includes a ratchet.]

[33. The instrument according to claim 29, wherein the drive handle includes a motor for imparting rotary motion to the drive shaft.]

[34. The instrument according to claim 29, further comprising a distal coupler for interchangeably coupling the instrument tip to the drive shaft.]

[35. The instrument according to claim 34, wherein the distal coupler includes a male-female socket joint disposed on the drive shaft and the instrument tip to removably connect the instrument tip to the drive shaft.]

[36. The instrument according to claim 29, wherein the instrument tip is an awl.]

[37. The instrument according to claim 29, wherein the instrument tip is a tap.]

[38. The instrument according to claim 29, wherein the instrument tip has a shaped end for mating with a workpiece to be rotated by said drive shaft.]

[39. The instrument according to claim 29, wherein the instrument tip is a drill bit.]

[40. The instrument according to claim 29, wherein the emitter array includes at least one LED array for emitting light signals.]

[41. The instrument according to claim 29, wherein the at least one LED array includes a base and a plurality of LED is emitters disposed on the base.]

[42. The instrument according to claim 29, wherein at least one bushing is provided in the guide member to reduce friction between the guide member and drive shaft.]

[43. A trackable medical instrument for use in a computer assisted image guided surgery system having a digitizer for tracking the position of the instrument in three dimensional space and a display providing an indication of the position of the instrument with respect to images of a body part taken preoperatively, the instrument comprising:

a guide member having a tracking device mounted thereon for being tracked by a digitizer;

a drive shaft contained within the guide member, the drive shaft having a longitudinal axis and a proximal and a distal end, the drive shaft being rotatable within the guide member while being fixable within the guide member in a direction of the longitudinal axis;

an instrument tip extending from the proximal end of the drive shaft; wherein the instrument tip rotates freely relative to the guide member while being fixable axially relative to the guide member; and a drive handle extending from the distal end of the drive shaft for guiding the instrument, including the guide member, and for imparting rotary motion to the drive shaft and the instrument tip independent of the guide member.]

[44. The instrument according to claim 43, wherein the tracking device includes a passive signal generator.]

[45. The instrument according to claim 44, wherein the instrument comprises at least one reflective surface for reflecting signals to be tracked by the digitizer.]

[46. The instrument according to claim 44, wherein the instrument comprises at least three reflective surfaces for reflecting signals to be tracked by the digitizer.]

[47. The instrument according to claim 43, further comprising a proximal coupler for interchangeably coupling the drive source to the drive shaft.]

[48. The instrument according to claim 47, wherein the proximal coupler comprises a male-female socket joint disposed on the drive shaft and the drive source to removably connect the drive source to the drive shaft.]

[49. The instrument according to claim 43, further comprising a distal coupler for interchangeably coupling the instrument tip to the drive shaft.]

[50. The instrument according to claim 49, wherein the distal coupler includes a male-female socket joint disposed on the drive shaft and the instrument tip to removably connect the instrument tip to the drive shaft.]

*51. A method to track a medical instrument system for use in a computer assisted image guided surgery system, comprising:*

*tracking a tracking device mounted on a guide member, wherein a drive shaft is contained within the guide member, the drive shaft having a proximal end and a distal end, the distal end having a first connector for interchangeably receiving a first instrument tip and a second instrument tip, wherein the first instrument tip is calibrated to the computer assisted image guided surgery system; and*

*recalibrating the second instrument to the computer assisted image guided surgery system after removing the first instrument tip from first connector and connecting the second instrument tip to the connector;*

*wherein the proximal end of the drive shaft has a second connector for interchangeably receiving at least one drive source for transmitting torque to the drive shaft.*

*52. The method of claim 51, further comprising:*

*operating the at least one drive source to cause rotation of the drive shaft relative to the guide member.*

*53. The method of claim 52, further comprising:*

*rotating the drive shaft within the guide member while having the drive shaft fixed in a direction of the longitudinal axis within the guide member.*

*54. A method to track a medical instrument system for use in a computer assisted image guided surgery system, comprising:*

*providing a guide member having a tracking device mounted thereon for being tracked; and*

*providing a drive shaft contained within the guide member, the drive shaft having a longitudinal axis, a first end and a second end, the drive shaft being rotatable within the guide member while being fixable within the guide member along the longitudinal axis, the first end of the drive shaft having a first connector for receiving at least one drive source for transmitting torque to the drive shaft for causing rotation of the drive shaft relative to the guide member, and the second end having at least one instrument tip.*

*55. The method of claim 54, further comprising:*

*connecting the drive source to the drive shaft, wherein the drive source is a drive handle.*

*56. The method of claim 54, further comprising:*

*permanently attaching the drive shaft and the at least one instrument tip.*

*57. The method of claim 54, further comprising:*

*permanently attaching at least the drive shaft and the at least one drive source.*

*58. The method of claim 54, further comprising:*

*permanently attaching all of the drive shaft, the at least one instrument tip, and the drive source.*

*59. The method of claim 54, further comprising:*

*providing bushings between the drive shaft and the guide member to allow smooth operation of the drive shaft.*

*60. The method of claim 54, further comprising:*

*entering information regarding dimensions of the at least one instrument tip into the computer.*

*61. The method of claim 54, further comprising:*

*providing at least one of a tap, an awl, a shaped tool, or a screw driver as the at least one instrument tip.*

*62. The method of claim 54, further comprising:*

*displaying images with a monitor;*

*connecting a reference arc to a patient; and*

*triangulating a position of at least one of the tracking device or the reference arc with a digitizer.*

*63. A method of configuring a trackable medical instrument for use with a surgical navigation system, comprising:*

*providing an instrument tip having a distal end;*

*configuring the instrument tip to couple to a drive shaft contained and rotatable within a guide member, wherein a tracking device is mountable to the guide member, wherein the drive shaft having a longitudinal axis has a shaft proximal end and a shaft distal end, wherein the shaft proximal end is adapted to receive a drive source and the shaft distal end is adapted to receive the instrument tip; and*

*fixing the drive shaft in relation to the guide member in a direction of the longitudinal axis relative to the distal end, wherein a rotation of the mountable tracking device relative to the instrument tip enables the distal end of the surgical implement to be tracked by the surgical navigation system.*

*64. The method of claim 63, wherein fixing the drive shaft in relation to the guide member in the direction of the longitudinal axis relative to the distal end maintains a constant distance between the tracking device and the distal end of the instrument tip.*

*65. The method of claim 63, wherein fixing the guide member in the direction along the longitudinal axis relative to the distal end enables both orientation in three-dimensional space of the instrument tip and a depth the distal end of the instrument tip has been inserted into a body part to be tracked by the surgical navigation system.*

*66. The method of claim 63, further comprising:*

*rotatably coupling the instrument tip to the guide member.*

*67. The method of claim 63, further comprising:*

*integrally forming the instrument tip and the guide member.*

*68. The method of claim 63, further comprising:*

*mounting the tracking device to the guide member.*

*69. The method of claim 63, further comprising:*

*coupling the drive source to the instrument tip.*

*70. The method of claim 69, further comprising:*

*providing the driver source to be a handle for holding with a hand.*

*71. The method of claim 69, wherein coupling the drive source to the instrument tip includes coupling the drive member to a proximal end of the instrument tip.*

* * * * *